United States Patent [19]

La Rosa

[11] 4,033,353

[45] July 5, 1977

[54] TRACHEOSTOMY TUBE

[75] Inventor: John La Rosa, Warwick, N.Y.

[73] Assignee: International Paper Company, New York, N.Y.

[22] Filed: Oct. 16, 1975

[21] Appl. No.: 623,115

[52] U.S. Cl. .................... 128/351; 128/349 BV
[51] Int. Cl.² ............... A61M 16/00; A61M 25/02
[58] Field of Search .......... 128/348, 349 R, 349 B, 128/349 BV, 350 R, 350 V, 351, DIG. 26; 285/12, 260, 423, DIG. 22

[56] References Cited

UNITED STATES PATENTS

| 954,519 | 4/1910 | Kelly | 128/361 |
|---|---|---|---|
| 2,765,792 | 10/1956 | Nichols | 128/351 |
| 2,786,469 | 3/1957 | Cohen | 128/351 |
| 2,860,372 | 11/1958 | Youthed | 285/260 X |
| 3,088,466 | 5/1963 | Nichols | 128/351 |
| 3,169,529 | 2/1965 | Zoenig | 128/351 |
| 3,236,236 | 2/1966 | Hudson | 128/351 X |
| 3,322,126 | 5/1967 | Rusch et al. | 128/351 |
| 3,334,631 | 8/1967 | Stebleton | 128/351 |
| 3,443,564 | 5/1969 | Oehmig | 128/351 |
| 3,461,877 | 8/1969 | Morch | 128/351 |
| 3,552,778 | 1/1971 | Muller | 285/276 X |
| 3,599,642 | 8/1971 | Tindel | 128/351 |
| 3,606,669 | 9/1971 | Kemble | 29/434 |
| 3,642,005 | 2/1972 | McGinnis | 128/351 |
| 3,659,612 | 5/1972 | Shiley et al. | 128/351 |
| 3,688,774 | 9/1972 | Akiyama | 128/351 |
| 3,720,210 | 3/1973 | Diettrich | 128/214.4 |
| 3,810,474 | 3/1974 | Cross | 128/351 |

Primary Examiner—Edgar S. Burr
Assistant Examiner—Paul T. Sewell
Attorney, Agent, or Firm—Finnegan, Henderson, Farabow & Garrett

[57] ABSTRACT

A tracheostomy tube, shaped to conform to the trachea, and including an inner and an outer cannula. The extremities of the cannulae inserted in the trachea are in frictional contact to prevent significant gas flow through the annular space between the cannulae. The opposite extremity of the outer cannula is shaped for connection to a respirator with the corresponding end of the inner cannula attached to an adaptive member through a nutating connection. The adaptive member is shaped at its inner end for connection to the outer cannula and at its outer end to a respirator. The outer cannula may include an inflatable cuff for sealing the cannulae within the trachea and a flexible neck flange for limiting the motion of the tracheostomy tube.

38 Claims, 6 Drawing Figures

TRACHEOSTOMY TUBE

FIELD OF THE INVENTION

This invention relates to tracheostomy tubes and in particular, a tracheostomy tube comprising an inner and outer cannula that allows attachment of a respirator to either the inne or outer cannula of the tracheostomy tube.

BACKGROUND OF THE INVENTION

Tracheostomy tubes are conventionally used to bypass obstructions in the trachea or provide a direct respiratory route to assist the respiration of the recipient of the device. A tracheostomy tube can be inserted through an incision in the trachea to provide respiratory access to the patient.

Early tracheostomy tubes were normally comprised of a single tube that required diligent care to prevent the obstruction of the airway by body fluids or mucous materials. In the event the single tube become clogged or obstructed, the tube would have to be removed and reinserted. This would require the attention of a doctor and an interruption in assisted respiration if the patient was receiving respiratory aid by means of a respirator.

In light of the problems with single tube tracheostomy devices, there are now tracheostomy tubes that have two concentric cannulae. Respiration normally passes through the inner cannula and in the event of a blockage in the tracheostomy tube, the inner cannula can be removed and cleared while the outer cannula provides a clear airway for the patient.

U.S. Pat. No. 3,569,612 Shiley et al. is typical of such a device where an inner and an outer cannula are placed within the trachea of the patient. The inner cannula may be connected to a respirator if respiratory assistance is required. If the inner cannula is obstructed, it can be removed from the outer cannula and the obstruction thereafter extracted from the inner cannula. During the time the inner cannula is removed, the patient breathes thorugh the outer cannula. No provision is made for attaching a respiratory to the outer cannula so that the patient may receive respiratory assistance while the inner cannula is removed.

A further problem with prior art devices is patient comfort. Preferably, the insertion of a tracheostomy tube into the trachea of the patient should provide as little discomfort as possible. Prior art devices being inherently rigid and unyielding do not meet the comfort requirements of the patient. While the prior art does include a flange that is vertically pivoted about the outer cannula, there is still a need to improve the adaptability of such devices to the various anatomical configurations of patients receiving tracheostomy tubes.

SUMMARY OF THE INVENTION

In accordance with the purpose of the invention as embodied and broadly described herein, the trachestomy tube of the invention comprises an outer cannula and an inner cannula disposed to fit removably within the outer cannula, the extremities of the cannulae inserted in the trachea being in frictional contact for preventing gas flow between the inner and outer cannula. The exterior extremity of the outer cannula is for connection to a respirator and the exterior extremity of the inner cannula is attached to an adaptive member through a nutating connection. The adaptive member having at its inner end means for connection to the outer cannula and its outer end means for connection to a respirator.

Preferably, the nutating connection comprises an exterior annular groove on the exterior extremity of the inner cannula that engages an interior annular ridge within the adaptive member. The ridge fits within the groove affixing the inner cannula to the adaptive member and allows limited relative movement therebetween.

It is also preferred that the outer cannula include an inflatable endotracheal cuff affixed to the exterior surface of the outer cannula adjacent its inner extremity for sealing the annular space between the cannula and the trachea wall to prevent passage of solids, liquids or gasses through that space.

It is further preferred that the means for connection of the outer cannula and the adaptive member to the respirator include annular anti-torque rings to prevent torque from being transmitted to the tracheostomy tube by rotation of the respirator tube on the cannula or adaptive member.

The present invention is inherently more comfortable than prior art devices due to the self-aligning nature of a multidirectional nutating connection between the inner and outer cannula. In addition, the present invention may also include a flexible neck flange mounted to the outer cannula that can conform to a configuration of the anatomy of the recipient. The combination of these features improves the patient performance of such a device and in conjunction with the added benefit of allowing connection of the outer cannula to a respirator during the removal of the inner cannula provides the invention with a significant improvement over the prior art.

Additional advantages of the invention will be set forth in part in the description which follows, and in part, will be obvious from the description, or may be learned by practice of the invention. The advantages of the invention may be realized and attained by means of the instrumentalities and combinations particularly pointed out in the appended claims.

BRIEF DESCRIPTION OF THE DRAWINGS

The invention consists of the novel parts, constructions, arrangements, combinations and improvements shown and described. The accompanying drawings which are incorporated in and constitute a part of the specification illustrate one embodiment of the invention and, together with the description, serve to explain the principles of the invention.

Of the Drawings.

DESCRIPTION OF THE PREFERRED EMBODIMENT

Figure 1:
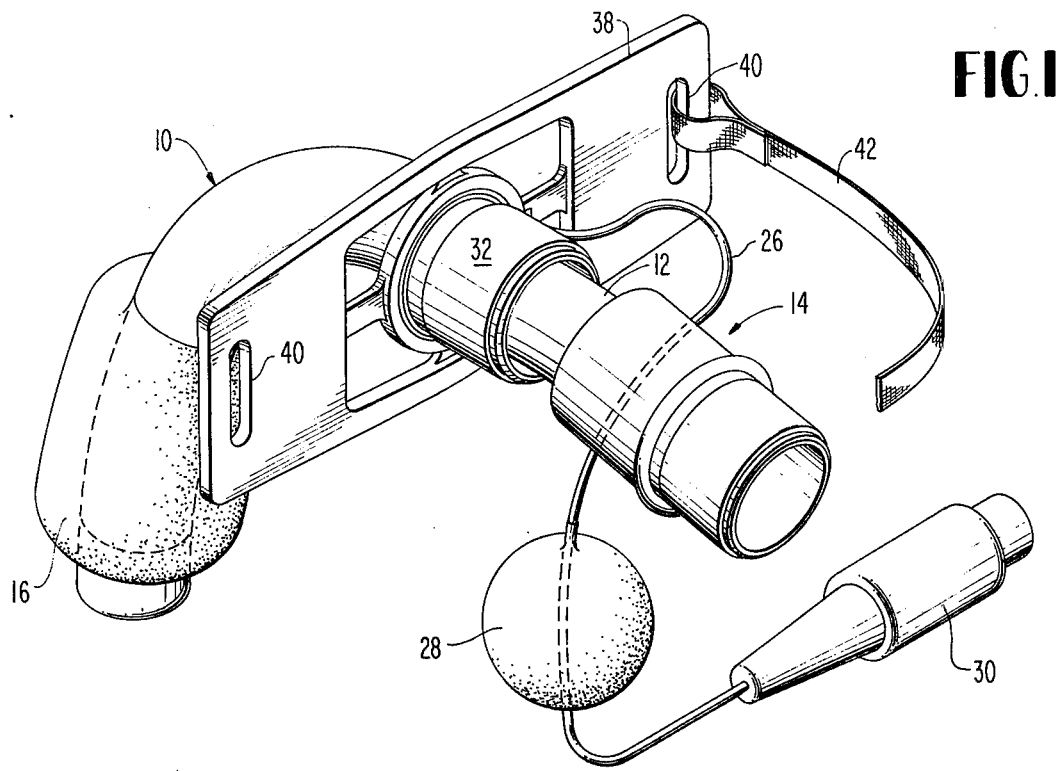
FIG. 1 is a perspective view of one embodiment of the tracheostomy tube assembly of the invention with the inner cannula partially extracted from the outer cannula.
Figure 2:
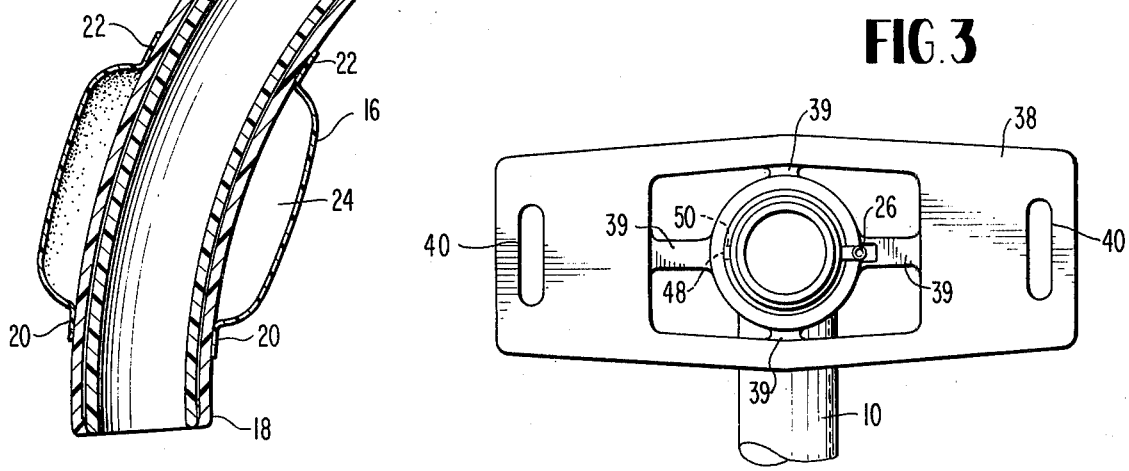
FIG. 2 is a cross-sectional view of the outer and inner cannulae of the tracheostomy tube of FIG. 1 and members attached thereto.

Reference will now be made in detail to the present preferred embodiment of the invention, an example of which is illustrated in the accompanying drawings. Referring now to FIGS. 1 and 2, it may be seen that the tracheostomy tube of the present invention is generally comprised of an outer cannula 10, an inner cannula 12 and an adaptive member 14.

In accordance with the invention, the outer cannula is disposed for insertion into the trachea of the patient to provide assistance in respiration. It is a primary function of the outer cannula to provide an alternate airway in the event the primary airway, the inner cannula 12, is removed from the tracheostomy tube.

As here embodied and most clearly depicted in FIG. 2, the outer cannula is curved to conform with the natural configuration of the trachea of the recipient. While anatomical differences between recipients require different degrees of curvature, the outer cannula is preferably flexible while having a curvature in the range of from 60° to 90°. The material used for the outer cannula should be biologically inert and be capable of contacting tissue of the recipient without promoting adverse reactions to the material. Preferably, the outer cannula consists of a polymeric material and particular success has been experienced with an embodiment of the invention consisting of polyvinylchloride. In embodiments of the invention where it is desired to make the position of the outer cannula externally detectable, an X-ray, opaque material such as Barium Sulphate may be incorporated into the device.

The size of the tracheostomy tube, and hence the outer cannula 10 is determined by the location of insertion of the device into the recipient. When the device is inserted into the recipient through an incision in the trachea, it is desired that the diameter of the outer cannula be approximately 0.5 inch.

The outer cannula 10 is inserted into the trachea of the recipient through the use of an obturator (not shown) which is removed after cannula insertion and the outer cannula 10 remains in the patient as long as the use of the tracheostomy tube is desired. As here embodied, the outer cannula 10 includes an inflatable endotracheal cuff 16. The cuff is affixed to the exterior surface of the outer cannula 10 adjacent the inner extremity 18 of the outer cannula 10. It is the function of the endotracheal cuff to form a pneumatic seal within the trachea of the recipient. The seal prevents backflow of air past the outer cannula to the location of insertion of the tracheostomy tube and other portions of the respiratory tract of the recipient that are not intended to receive the infusion of air through the tracheostomy tube, and to prevent passage of liquids or solids into the recipient's bronchi and lungs.

Figure 3:
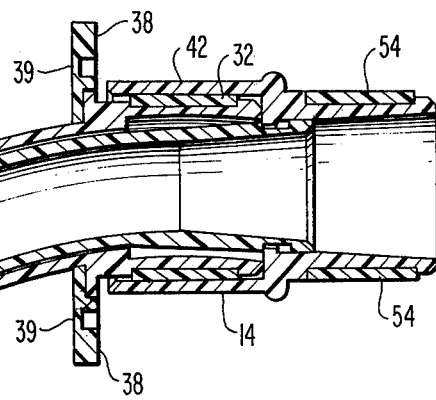
FIG. 3 is an end view of the embodiment of FIGS. 1 and 2 showing the structure of the flexible neck flange and the arrangement of the aligning key and inflation line.

As here embodied, the endotracheal cuff 16 is comprised of a tubular elastic member. The tubular elastic member 16 is sealed at each of its extremities 20 and 22, respectively, to the outer surface of the outer cannula 10. As previously described, the endotracheal cuff 16 is located adjacent the inner extremity 18 of the outer cannula 10. The interior 24 of the tubular elastic member 16 is in flow communication with a source of pneumatic pressure. As here embodied and best seen in FIGS. 1 and 3, the means for providing flow communication to the endotracheal cuff 16 comprise a tube 26 within a groove in the exterior wall of the outer cannula 10.

As depicted in FIG. 1, the tube 26 is also in flow communication with an inflatable member 28 that indicates the condition of the endotracheal cuff 16. The application of pneumatic pressure to the tube 26 inflates the member 28 and since the member 28 is external from the trachea of the patient, the condition of the member 28 also indicates the condition of the endotracheal cuff 16.

The endotracheal cuff and the inflatable member 28 are both subjected to pneumatic pressure through an inflation valve 30. Preferably, the inflation valve 30 is self-sealing and allows introduction of pneumatic pressure within the endotracheal cuff 16 and the inflatable member 28 in flow communication with the valve. The self-sealing valve 30 may be simply a member providing flow communication through the inflatable members by means of a membrane that can be pierced by hypodermic needle or the valve 30 may simply adapt to a source of pneumatic pressure to provide the inflation of the endotracheal cuff and the indicating inflatable member. The self-sealing valve 30 may include means for deflating the endotracheal cuff 16 and the indicating member 28.

While the interior extremity 18 of the outer cannula 10 preferably includes the endotracheal cuff 16, the exterior extremity of the outer cannula has means for connection to a respirator (not shown). As here embodied and most clearly depicted in FIG. 5, the means for connection to a respirator comprise a fitting on the extremity of the outer cannula.

It is the function of the fitting to interface with means connecting the outer cannula 10 to a respirator thereby allowing respiratory assistance to the recipient of the tracheostomy tube while the inner cannula 12 is removed from the device. Since such devices are periodically subjected to blockage and require extraction of the inner cannula, the capability of the outer cannula as being adaptable to receive a connection to a respirator allows the recipient of the device to receive respiratory assistance whether or not the inner cannula is in place.

Figure 5:
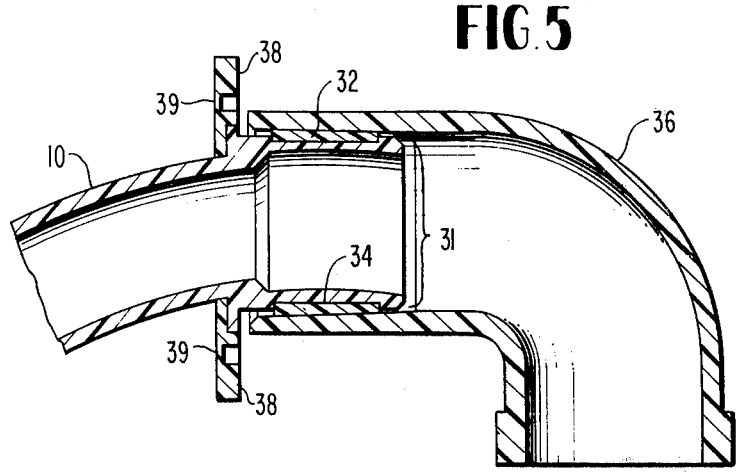
FIG. 5 is a partial, vertical, cross-section through the outer cannula with the inner cannula removed showing the attachment of a respirator fitting to the outer cannula.

As here embodied, the means for connection to a respirator as depicted in FIG. 5 is a fitting 31 including an anti-torque ring 32. The anti-torque ring 32 is disposed in a groove 34 in the exterior extremity of the outer cannula 10. It is the function of the anti-torque ring to prevent torque from being transmitted through the connection to the respirator (shown here as elbow fitting 36) to the patient through the outer cannula 10. In the embodiment shown, rotation of the elbow fitting 36 results in the rotation of the anti-torque ring 32 rather than in the application of torque to the exterior extremity of the outer cannula 10. This feature enhances patient comfort and allows movement of the recipient of the device and the respirator connection without attendant discomfort due to the movement.

Preferably, the outer cannula 10 includes a neck flange for limiting the motion of the tracheostomy tube at the site of insertion of the tube. As here embodied and most clearly depicted in FIGS. 1, 3 and 5, a neck flange 38 is attached to the outer cannula 10 adjacent the exterior extremity. Preferably, the neck flange 38 is comprised of a plurality of flexible webs 39 that allow limited motion of the outer portion of the neck flange without transmitting such motion to the outer cannula.

The outer portion of the neck flange 38 is preferably elongated and includes slots 40 proximate the extremities of the outer portion. The slots are disposed to receive means for immobilizing the neck flange. As here embodied, and best depicted in FIG. 1, the means for immobilizing the neck flange is, simply a strap 42 that passes through the slots 40 and around the recipient of the device thereby immobilizing it at the site of insertion. The flexibility of the neck flange 38 allows for the anatomical differences of the recipients of such a device and also allows limited movement of the recipient without attendant patient discomfort.

In accordance with the invention, an inner cannula is disposed to fit removably within the outer cannula. As here embodied, the inner cannula 12 is tubular and is generally concentric with the outer cannula and annularly displaced therefrom. The annular space between the two cannulae also enhances the flexible of the assembled device by reducing friction therebetween. Preferably, the inner and outer cannula include means to prevent the gas flow between the cannulae. As here embodied and most clearly depicted in FIG. 2, the inside diameter of the outer cannula 10 at the inner extremity 18 is equal to the outside diameter of the inner cannula 12 at its interior extremity. The two cannulae being in frictional, sealing contact thereby prevent significant gas flow between the inner and outer cannula. It is the function of the inner cannula to be the primary means of air flow through the tracheostomy tube to the recipient and the outer cannula is the secondary means for providing air flow to the recipient. The outer cannula is only utilized for air flow when the inner cannula is removed.

In accordance with the invention, an adaptive member has a first end removable affixed to the exterior extremity of the outer cannula, the second end of the adaptive member having means for connection to a respirator with the adpative member including an interior nutating connection to the inner cannula.

Figure 4:
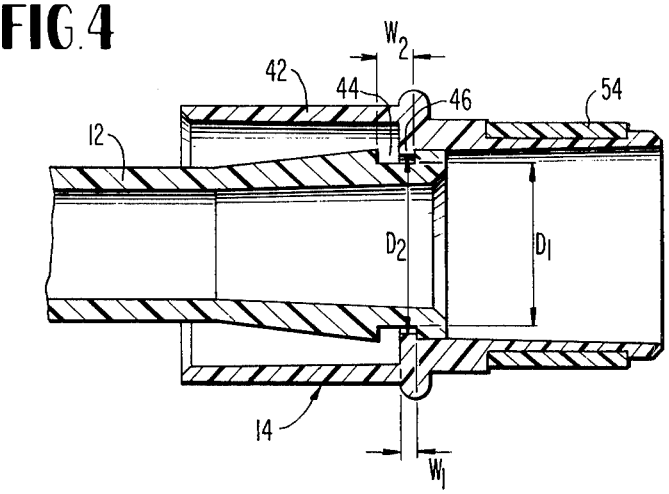
FIG. 4 is an enlarged partial, vertical, cross-section illustrating the nutating connection between the adaptive member and the inner cannula.
Figure 6:
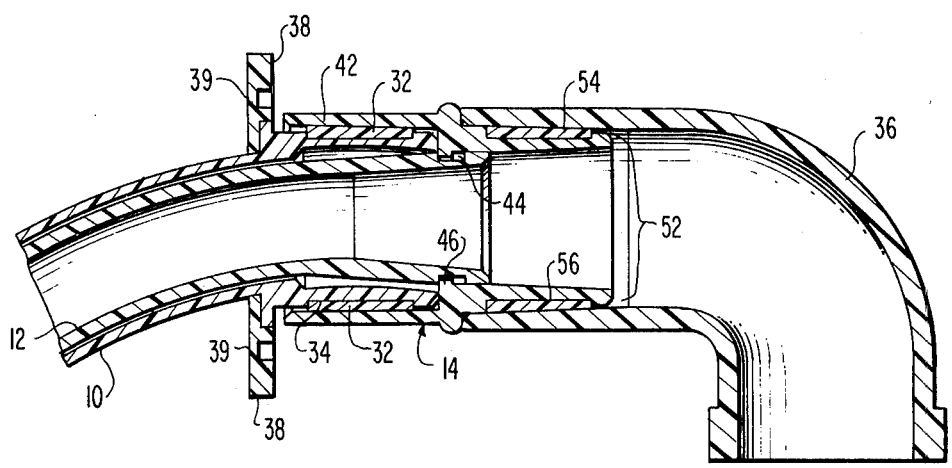
FIG. 6 is a partial, vertical, cross-section through the outer cannula with the inner cannula in place illustrating the attachment of a respirator fitting to the adaptive member connected to the inner cannula.

As here embodied and most clearly depicted in FIGS. 4 and 6, the adaptive member 14 has one end having a connection 42 approximating that of the respirator fitting, e.g., elbow fitting 36, that fits on the external extremity 31 of the outer cannula. The adaptive member is connected to the inner cannula 12 through a nutating connection, allowing limited relative movement between the adaptive member 14 and the inner cannula 12.

As here embodied and best illustrated in FIG. 4, the nutating connection is comprised of an exterior annular groove 44 on the exterior extremity of the inner cannula and an interior annular ridge 46 within the adaptive member 14. The ridge 46 fits within the groove 44 affixing the inner cannula 12 to the adaptive member 14. As is depicted in FIG. 4, the annular ridge 46 preferably has a width ($W_1$) significantly less than the width ($W_2$) of the annular groove 44 in the exterior of the inner cannula 12. This allows axial and radial movement of the inner cannula 12 in relation to the adaptive member 14.

Preferably, the inside diameter ($D_1$) of the annular groove 44 in the inner cannula is significantly less than the inside diameter ($D_2$) of the opening defined by the ridge 46 in the adaptive member 14. The clearance between the two members allowing limited movement between the inner cannula and the adaptive member provides the nutating movement. It is the function of the nutating connection to allow relative motion between the inner cannula and the adaptive member of the tracheostomy tube thereby enhancing patient comfort while wearing such a device and allowing the device to conform to anatomical differences between the recipients.

Preferably, the adaptive member includes means for preventing rotation of the inner cannula within the adaptive member. As here embodied and most clearly depicted in FIG. 3, the rotation preventing means comprise an aligning key 48 on the adaptive member 14 that is received by a slot 50 within the inner cannula 12. It is further preferred that the aligning key 48 and the slot 50 fit together in a manner that allows the nutating connection to conform to minor changes in configuration of the tracheostomy tube while still preventing substantial rotation of the inner cannula 12 within the adaptive member 14.

The adaptive member 14 has a second end that is disposed to connect to a standard respirator fitting. As here embodied and depicted in FIG. 6, the second end of the adaptive member is fitting 52. The fitting 52 includes an annular anti-torque ring 54 similar to that on the external end extremity of the outer cannula 10. The anti-torque ring 54 on the second end of the adaptive member is free to rotate within groove 56 about the adaptive member 14 to prevent the application of torque from the respirator fitting 36 to the adaptive member 14 that would be transmitted to the outer cannula 10 through the aligning key 48 and ultimately to the trachea of the recipient.

The second end of the adaptive member 14 and the external extemity 31 of the outer cannula are both disposed to receive the appropriate respirator fitting depicted in the figures as elbow fitting 36. Therefore, the tracheostomy tube of the present invention can provide respiratory assistance with the inner cannula 12 in place or by transfer of the elbow fitting 36 to the outer extremity 31 of the outer cannula 10 upon removal of the adaptive member 14 and the inner cannula 12, the respiratory assistance can be continued during removal and cleaning of the inner cannula 12.

The tracheostomy tube of the present invention in the preferred embodiment provides for superior patient comfort and adaptability due to the combination of numerous means of providing allowance for anatomical differences and relative motion of the component parts. The flexible neck flange 38, the anti-torque rings 32 and 54 on the connections, the annular spacing of the cannulae and the nutating connection of the inner cannula 12 to the adaptive member 14 combine to make the present invention readily adaptable to anatomical differences of recipients of the device and allow limited movement of the recipient without attendant discomfort due to the structural rigidity of the tracheostomy tube.

It will be apparent to those skilled in the art that various modifications and variations could be made in the tracheostomy tube as disclosed herein without departing from the scope of the invention as defined by the appended claims.

What is claimed is:

1. A tracheostomy tube comprising:
    an outer cannula for insertion into a trachea, said outer cannula having interior and exterior extremities, said exterior extremity of said outer cannula having means for connection to a respirator;

an inner cannula disposed to fit removably within said outer cannula, said inner cannula having interior and exterior extermities;

means for preventing significant gas flow between said inner and outer cannulae; and an adaptive member having an interior nutating connection to said inner cannula, said adaptive member also including at its inner end means for connection to said exterior extremity of said outer cannula and at its outer end means for connection to a respirator, said nutating connection comprising an exterior annular groove on the exterior extremity of said inner cannula and an interior annular ridge within said adaptive member, said ridge fitting within said groove and connecting said inner cannula to said adaptive member while allowing limited movement therebetween, the width of said groove being significantly greater than the width of said ridge and the inside diameter of said groove being significantly less than the diameter of the inner surface of said annular ridge.

2. The tracheostomy tube of claim 1 wherein said inner cannula is generally concentric with said outer cannula with the inside diameter of the outer cannula at the interior extremity of said outer cannula equal to the outside diameter of the interior extremity of said inner cannula and in contact therewith for preventing significant gas flow between said inner cannula and said outer cannula.

3. The tracheostomy tube of claim 1 including an inflatable endotracheal cuff, said cuff being affixed to the exterior surface of said outer cannula adjacent its inner extremity.

4. The tracheostomy tube of claim 3 wherein said endotracheal cuff is comprised of a tubular elastic member, said tubular elastic member being sealed at each of its extremities, and wherein said tracheostomy tube includes means for flow communication between the interior of said tubular elastic member and a source of pneumatic pressure.

5. The tracheostomy tube of claim 4 wherein said communicating means comprise a tube within a groove in the exterior wall of said outer cannula.

6. The tracheostomy tube of claim 4 including an inflatable member, said inflatable member being in flow communication with said inflatable cuff, said inflatable member indicating the inflation condition of said endotracheal cuff.

7. The tracheostomy tube of claim 6 wherein said flow communicating means includes a sefl-sealing valve, said self-sealing valve allowing introduction of pneumatic pressure within said endotracheal cuff and said inflatable member in flow communication therewith.

8. The tracheostomy tube of claim 1 wherein the means for connecting said outer cannula to a respirator comprises a fitting including an annular anti-torque ring attached thereto, said anti-torque ring being free to rotate around said outer cannula.

9. The tracheostomy tube of claim 1 wherein the means for connecting the outer end of said adaptive member to a respirator comprises a fitting including an annular anti-torque ring attached thereto, said anti-torque ring being free to rotate around said adaptive member.

10. The tracheostomy tube of claim 1 wherein said adaptive member includes means for preventing substantial rotation of said inner cannula within said adaptive member.

11. The tracheostomy tube of claim 1 including an elongated flexible neck flange attached to said outer cannula, said neck flange comprising a plurality of flexible webs having slots proximate the extremities thereof, said slots being adapted to receive means for immobilizing said neck flange at the site of insertion of said tube.

12. A tracheostomy tube comprising:

an outer cannula for insertion into a trachea, said outer cannula having interior and exterior extremities, said exterior extremity of said outer cannula having means for connection to a respirator;

an inner cannula disposed to fit removable within said outer cannula, said inner cannula having interior and exterior extremities;

means for preventing significant gas flow between said inner and outer cannulae; and an adaptive member having an interior nutating connection to said inner cannula, said adaptive member also including at its inner end means for connection to said exterior extremity of said outer cannula and at its outer end means for connection to a respirator, said adaptive member including means for preventing substantial rotation of said inner cannula within said adaptive member, said rotation preventing means comprising an aligning key on said adaptive member and slot on said inner cannula disposed to receive said key.

13. The tracheostomy tube of claim 12 wherein said nutating connection comprises an exterior annular groove on the exterior extremity of said inner cannula and an interior annular ridge within said adaptive member, said ridge fitting within said groove and connecting said inner cannula to said adaptive member while allowing limited movement therebetween.

14. The tracheostomy tube of claim 13 wherein the width of said groove is significantly greater than the width of said ridge and the inside diameter of said groove is significantly less than the diameter of the inner surface of said annular ridge.

15. The tracheostomy tube of claim 12 wherein said inner cannula is generally concentric with said outer cannula with the inside diameter of the outer cannula at the interior extremity of said outer cannula equal to the outside diameter of the interior extremity of said inner cannula and in contact therewith for preventing significant gas flow between said inner cannula and said outer cannula.

16. The tracheostomy tube of claim 12 including an inflatable endotracheal cuff, said cuff being affixed to the exterior surface of said outer cannula adjacent its inner extremity.

17. The tracheostomy tube of claim 16 wherein said endotracheal cuff is comprised of a tubular elastic member, said tubular elastic member being sealed at each of its extremities, and wherein said tracheostomy tube includes means for flow communication between the interior of said tubular elastic member and a source of pneumatic pressure.

18. The tracheostomy tube of claim 17 wherein said communicating means comprise a tube within a groove in the exterior wall of said outer cannula.

19. The tracheostomy tube of claim 17 including an inflatable member, said inflatable member being in flow communication with said inflatable cuff, said inflatable member indicating the inflation condition of said endotracheal cuff.

20. The tracheostomy tube of claim 19 wherein said flow communicating means includes a self-sealing valve, said self-sealing valve allowing introduction of pneumatic pressure within said endotracheal cuff and said inflatable member in flow communication therewith.

21. The tracheostomy tube of claim 12 wherein the means for connecting said outer cannula to a respirator comprises a fitting including an annular anti-torque ring attached thereto, said anti-torque ring being free to rotate around said outer cannula.

22. The tracheostomy tube of claim 12 wherein the means for connecting the outer end of said adaptive member to a respirator comprises a fitting including an annular anti-torque ring attached thereto, said anti-torque ring being free to rotate around said adaptive member.

23. The tracheostomy tube of claim 12 including an elongated flexible neck flange attached to said outer cannula, said neck flange comprising a plurality of flexible webs having slots proximate the extremities thereof, said slots being adapted to receive means for immobilizing said neck flange at the site of insertion of said tube.

24. A tracheostomy tube comprising:
an outer cannula for insertion into a trachea and having interior and exterior extremities;
an inner cannula removably disposed within said outer cannula, said inner cannula having interior and exterior extremities;
an adaptive member, means providing an interior nutating connection between said inner cannula and said adaptive member, said adaptive member including at its inner end means for connection to said exterior extremity of said outer cannula and at its outer end means for connection to a respirator, said exterior extremity of said outer cannula having means for connection to a respirator to enable air flow through said outer cannula when said inner cannula is removed; and
means at a location spaced from said adaptive member and along said inner and outer cannulae for preventing significant gas flow between said inner and outer cannulae.

25. The tracheostomy tube of claim 24 wherein said nutating connection comprises an exterior annular groove on the exterior extremity of said inner cannula and an interior annular ridge within said adaptive member, said ridge fitting within said groove and connecting said inner cannula to said adaptive member while allowing limited movement therebetween.

26. The tracheostomy tube of claim 25 wherein the width of said groove is significantly greater than the width of said ridge and the inside diameter of said groove is significantly less than the diametr of the inner surface of said annular ridge.

27. The tracheostomy tube of claim 24 wherein said inner cannula is generally concentric with said outer cannula with the inside diameter of the outer cannula at the interior extremity of said outer cannula equal to the outside diameter of the interior extremity of said inner cannula and in contact therewith for preventing significant gas flow between said inner cannula and said outer cannula.

28. The tracheostomy tube of claim 24 including an inflatable endotracheal cuff, said cuff affixed to the exterior surface of said outer cannula adjacent its inner extremity.

29. The tracheostomy tube of claim 28 wherein said endotracheal cuff is comprised of a tubular elastic member, said tubular elastic member being sealed at each of its extremities, and wherein said tracheostomy tube includes means for flow communication between the interior of said tubular member and a source of pneumatic pressure.

30. The tracheostomy tube of claim 29 wherein said communicating means comprises a tube within a groove in the exterior wall of said outer cannula.

31. The tracheostomy tube of claim 29 including an inflatable member, said inflatable member being in flow communication with said inflatable cuff, said inflatable member indicating the inflation condition of said endotracheal cuff.

32. The tracheostomy tube of claim 31 wherein said flow cummunicating means includes a self-sealing valve, said self-sealing valve allowing introduction of pneumatic pressure within said endotracheal cuff and said inflatable member in flow communication therewith.

33. The tracheostomy tube of claim 24 wherein the means for connecting said outer cannula to a respirator comprises a fitting including an annular anti-torque ring attached thereto, said anti-torque ring being free to rotate around said outer cannula.

34. The tracheostomy tube of claim 24 wherein the means for connecting the outer end of said adaptive member to a respirator comprises a fitting including an annular anti-torque ring attached thereto, said anti-torque ring being free to rotate around said adaptive member.

35. The tracheostomy tube of claim 24 wherein said adaptive member includes means for preventing substantial rotation of said inner cannula within said adaptive member.

36. The tracheostomy tube of claim 35 wherein said rotation preventing means comprise an aligning key on said adaptive member and a slot on said inner cannula disposed to receive said key.

37. The tracheostomy tube of claim 24 including an elongated flexible neck flange attached to said outer cannula, said neck flange comprising a plurality of flexible webs having slots proximate the extremities thereof, said slots being adapted to receive means for immobilizing said neck flange at the site of insertion of said tube.

38. The tracheostomy tube of claim 24 wherein said respirator connection means on said outer cannula and said respirator connection means on said adaptive member have substantially identical external configurations for connection of either the outer cannula or adaptive member to a common respirator.

* * * * *

UNITED STATES PATENT AND TRADEMARK OFFICE
CERTIFICATE OF CORRECTION

PATENT NO. : 4,033,353
DATED : July 5, 1977
INVENTOR(S) : JOHN LA ROSA

It is certified that error appears in the above-identified patent and that said Letters Patent are hereby corrected as shown below:

Column 7, claim 7, line 53, change "sefl" to --self--.

Column 8, claim 12, line 17, change "removable" to --removably--.

Column 9, claim 26, line 58, change "diametr" to --diameter--.

Column 10, claim 29, line 14, after "tubular" insert --elastic--.

Signed and Sealed this

Eleventh Day of October 1977

[SEAL]

Attest:

RUTH C. MASON
*Attesting Officer*

LUTRELLE F. PARKER
*Acting Commissioner of Patents and Trademarks*